United States Patent [19]

Penska et al.

[11] Patent Number: 5,851,544
[45] Date of Patent: Dec. 22, 1998

[54] COSMETIC SKIN OR HAIR CARE COMPOSITIONS CONTAINING FLUOROCARBONS INFUSED WITH CARBON DIOXIDE

[75] Inventors: Christine Penska, Park Ridge; Uma Santhanam, Tenafly; Stephan Habif, Demarest, all of N.J.

[73] Assignee: Chesebrough-Pond's USA Co., Division of Conopco, Inc., Greenwich, Conn.

[21] Appl. No.: 993,294

[22] Filed: Dec. 18, 1997

[51] Int. Cl.$^6$ ........................................ A61K 7/48
[52] U.S. Cl. .......................... 424/401; 424/59; 424/701; 424/70.27; 514/746; 514/759; 514/761; 514/844; 514/931; 514/938
[58] Field of Search ............................ 424/401, 59, 70.1, 424/70.27; 514/746, 759, 761, 844, 937, 938

[56] References Cited

U.S. PATENT DOCUMENTS

| | | | |
|---|---|---|---|
| 4,569,784 | 2/1986 | Moore | 252/315 |
| 4,879,062 | 11/1989 | Moore | 252/315 |
| 5,451,395 | 9/1995 | Murray et al. | 424/70.11 |
| 5,498,421 | 3/1996 | Grinstaff et al. | 424/450 |
| 5,580,550 | 12/1996 | Gough et al. | 424/70.11 |
| 5,665,382 | 9/1997 | Grinstaff et al. | 424/450 |

FOREIGN PATENT DOCUMENTS

| | | |
|---|---|---|
| 0 275 695 | 7/1988 | European Pat. Off. |
| 934570 | 6/1993 | South Africa. |
| 934571 | 6/1993 | South Africa. |
| 946064 | 8/1994 | South Africa. |

OTHER PUBLICATIONS

Artmann et al., "Oxygen in the skin a new parameter of skin ageing," SOFW 119/15, pp. 942–948 (1993).
Hartmann et al., "Effect of carbon dioxide–enriched water and fresh water on the cutaneous microcirculation and oxygen tension in the skin of the foot," *Angiology*, vol. 48, pp.337–343 (1997).
Ryan et al., "The Development of Adipose Tissue and its Relationship to the Vascular System," *Clinics in Dermatology*, vol. 7, No. 4, pp. 1–7, Oct.–Dec. (1989).
S. Curri et al., "Cellulite and Fatty Tissue Microcirculation," *Cosmetics & Toiletries*, vol. 108, pp. 51–58, Apr. (1993).
*Medline Abstract* of Goldman et al., "Transcutaneous pO2 of the scalp in male pattern baldness; a new piece to the puzzle.," *Plast–Reconstr–Surg.* 1996–May; 97(6):1109–16.

*Primary Examiner*—Jyothsna Venkat
*Attorney, Agent, or Firm*—Rimma Mitelman

[57] ABSTRACT

Cosmetic skin or hair care compositions containing a liquid, inert, hydrophobic fluorocarbon infused with carbon dioxide. The compositions increase blood flow to the skin, thus increasing endogenous oxygen and nutrient delivery to the skin.

3 Claims, No Drawings

COSMETIC SKIN OR HAIR CARE COMPOSITIONS CONTAINING FLUOROCARBONS INFUSED WITH CARBON DIOXIDE

FIELD OF THE INVENTION

Cosmetic compositions containing an inert, liquid, hydrophobic fluorocarbon infused with carbon dioxide.

BACKGROUND OF THE INVENTION

Oxygen is used by skin cells to produce energy to fuel cellular processes such as proliferation and production of extracellular matrix substances both of which are essential for maintaining healthy, young looking skin. Oxygen levels in the skin are lower than in other parts of the body and are known to decrease further with age. See e.g. Artmann et.al. "Oxygen in the skin a new parameter of skin ageing," *SOFW* 119/15, pp. 942–48 (1993). Thus, skin care compositions which increase skin oxygen levels are desirable.

One way of increasing skin oxygen levels is by increasing blood flow to the skin. Immersion of the skin in carbon dioxide enriched water has previously been shown to increase blood flow and therefore oxygen delivery to the skin. See e.g. Hartmann et.al. "Effect of carbon dioxide-enriched water and fresh water on the cutaneous microcirculation and oxygen tension in the skin of the foot," *Angiology*, vol.48,pp.337–43(1997).

Ryan et al. and Curri et al. describe that increased blood flow to the skin may be beneficial in the treatment of cellulite. See Ryan et al. "The Development of Adipose Tissue and its Relationship to the Vascular System," *Clinics in Dermatology*, Volume 7, Number 4, pp. 1–7, October––December (1989), and S. Curri "Cellulite and Fatty Tissue Microcirculation," *Cosmetics & Toiletries*, vol. 108, pp. 51–58, April (1993).

Fluorocarbons are safe, chemically inert compounds which are capable of dissolving large quantities of carbon dioxide gas. South African Patent Applications 934570, 934571 and 946064 (all to Lancaster) disclose that fluorocarbons containing oxygen can deliver oxygen to the skin via topical application. Such exogenous delivery of oxygen, however, has several important drawbacks. Topical treatment with oxygen does not increase blood flow to the skin (because oxygen is not a vasodilator) and, therefore, would not increase delivery of nutrients from the blood to skin. Also, oxygen is not safe to work with, because it is highly flammable, so it presents manufacturing challenges and an increase in cost. In addition, products containing oxygen do not allow a co-presence of agents that are sensitive to oxidation (i.e. antioxidants or retinoids) because such agents are unstable in the presence of oxygen.

Some cosmetic products, mainly antiperspirants, employ fluorocarbon gas, sometimes in mixtures with carbon dioxide, as a propellant. See e.g. EP 0 275 695. By contrast, skin care compositions in the present invention contain liquid fluorocarbons.

Cosmetic products for washing or styling of hair containing liquid fluorocarbons are also known. See e.g., Murray et al. U.S. Pat. No. 5,451,395 or Gough et al., U.S. Pat. No. 5,580,550.

Moore (U.S. Pat. Nos. 4,879,062 and 4,569,784) discloses gels containing perfluorocarbons and oxygen for treatment of wounds, bruises and irritations. Moore describes perfluorocarbons in the Background of the Invention section as substances capable of transporting inert gases such as oxygen, nitrogen, carbon dioxide, and air but the only gas in Moore's compositions is oxygen. Furthermore, Moore does not address the problems of either increasing the blood flow to skin or increasing endogenous oxygen level in skin. Moore does not teach cosmetic skin care compositions aimed at delivering anti-aging benefits to an intact, non-wounded skin. Rather, Moore's compositions are medicinal treatment compositions aimed at delivering exogenous oxygen and have the drawbacks associated with exogenous oxygen delivery as described above. Moore's compositions do not have the same mode of action and do not achieve the same results as the present invention.

SUMMARY OF THE INVENTION

The present invention includes a cosmetic skin or hair care composition comprising:

i) from about 0.1% to about 70%, by weight of the composition, of a fluorocarbon infused with carbon dioxide; and ii) a cosmetically acceptable vehicle;

wherein the fluorocarbon is inert, liquid at 25C., and hydrophobic.

The present invention also includes a method of delivering endogenous oxygen to skin, the method comprising applying to skin the inventive composition.

The inventive composition and method improve blood flow and circulation to skin and, consequently, improve supply of endogenous oxygen to skin. The increased blood flow may in turn result in reduced appearance of wrinkles and aged or photoaged skin, reduced signs of cellulite, improved skin color, improved condition of hair roots, improvement in skin's radiance and clarity and finish, and an overall healthy and youthful appearance of the skin.

DETAILED DESCRIPTION OF THE INVENTION

Except in the operating and comparative examples, or where otherwise explicitly indicated, all numbers in this description indicating amounts of material or conditions of reaction, physical properties of materials and/or use are to be understood as modified by the word "about." All amounts are by weight of the composition, unless otherwise specified.

The term "skin" as used herein includes the skin on the body, face and scalp.

The inventive compositions contain fluorocarbons which are fluorinated compounds that may or may not contain heteroatoms such as nitrogen, oxygen, sulfur, or another halogen. The fluorocarbons of the invention are dense, inert, hydrophobic liquids with a high capacity for dissolving carbon dioxide or oxygen (the more fluorinated the fluorocarbon the higher its capacity for dissolving a gas). Moreover, for the purpose of the invention fluorocarbons will be selected so that they are liquid (not gas and not solid) at room temperature, i.e. their boiling point is higher than 40 C. and preferably higher than 60 C. Thus, in practice fluorocarbons of the invention will have at least 6 carbon atoms and preferably 8 to 10 carbon atoms. Within these conditions, fluorocarbons have generally a low viscosity so that they are pourable like water or fluid oils used as emollients for cosmetic purpose.

Preferably, the fluorocarbons included in the inventive compositions are not charged (i.e., non-ionic), because non-charged fluorocarbons are more inert and also should deliver $CO_2$ better. The fluorocarbons of the invention can have straight chains (e.g., perfluorooctane, perfluorodecane), or may contain some ring structures (perfluorodecalin), they may contain heteroatoms such as other halogens (perfluorooctylbromide, perfluorodecylbromide, perfluorooctyliodide), nitrogen (perfluorotripropylamine, perfluoro-tributylamine), or hydrogen (bis-(F-butyl)-ethene or F-44E). Preferably, the fluorocarbon of the invention is a perfluorinated ether (e.g., perfluoro-polymethylisopropyl ether sold under tradenames of Fomblin or Aflunox 100), because perfluorinated ethers are relatively cheaper and commercially available.

The inventive compositions contain from 0.1% to 70%, preferably from 0.1% to 30%, most preferably (in order to maximize the efficacy/cost ratio) from 1% to 15% of fluorocarbon. The weight of the fluorocarbon remains essentially the same when it is infused with carbon dioxide.

According to the present invention a fluorocarbon is infused with carbon dioxide, preferably in a $CO_2$ atmosphere (e.g., under a $CO_2$ blanket) either before or after the fluorocarbon is incorporated into a final composition. In the most preferred embodiment of the invention, the fluorocarbon and the rest of the composition are each infused with carbon dioxide, under a $CO_2$ blanket, and then mixed with each other, under a $CO_2$ blanket. The infusion with carbon dioxide is attained by bubbling the gas through the fluorocarbon.

It is advantageous to infuse the fluorocarbon prior to its incorporation in a final composition due to the easier carbonation when bubbling through a low viscosity fluid rather than through a more viscous final composition. To maximize carbon dioxide delivery, infusion of carbon dioxide is done preferably until the fluorocarbon is totally saturated with carbon dioxide.

The fluorocarbon in the inventive composition carries typically 50% to 250%, preferably from 100 to 250%, most preferably from 140 to 250% its volume in carbon dioxide at 37 C.

The inventive compositions also include a cosmetically acceptable vehicle or a carrier which is inert, usually an ingredient present in the highest amounts, and functioning to deliver the fluorocarbon.

Vehicles other than or in addition to water can include liquid or solid emollients, solvents, humectants, thickeners and powders.

The cosmetically acceptable vehicle will usually form from 5% to 99.9%, preferably from 25% to 80% by weight of the composition, and can, in the absence of other cosmetic adjuncts, form the balance of the composition.

According to the present invention, the vehicle is preferably at least 50% water, by weight of the vehicle. The inventive compositions are preferably oil-water emulsions, to minimize carbon dioxide escape and/or the fluorocarbon evaporation. In the oil-in-water emulsions, fluorocarbon is dispersed as discrete droplets in an aqueous phase, minimizing fluorocarbon's direct contact with the atmosphere. In the preferred oil-in-water emulsions according to the present invention, water comprises at least 50%, most preferably from 60 to 80%.

Optional Skin Benefit Materials and Cosmetic Adjuncts
Cosmetic Skin Care Compositions The preferred compositions according to the present invention are cosmetic compositions for the treatment of skin aiming to achieve anti-aging benefits. Such compositions preferably include a sunscreen, to further minimize aging, wrinkling and photodamage to skin which result from exposure of skin to harmful UV-A and UV-B rays.

Illustrative compounds are the derivatives of PABA, cinnamate and salicylate. For example, octyl methoxycinnamate and 2-hydroxy-4-methoxy benzophenone (also known as oxybenzone) can be used. Octyl methoxycinnamate and 2-hydroxy-4-methoxy benzophenone are commercially available under the trademarks, Parsol MCX and Benzophenone-3, respectively. For optimal UV-A protection, the compositions may include avobenzone commercially available under the trademark Parsol 1789, and/or a physical sunscreen which offers broad spectrum protection such as titanium dioxide or zinc oxide. The exact amount of sunscreen employed in the emulsions can vary depending upon the degree of protection desired from the sun's UV radiation and the identity of the sunscreen employed.

Generally, the amount of the sunscreen in the inventive compositions for cosmetic skin care is in the range of from 0.1% to 25%. With regard to the individual sunscreen agents, the amounts are as follows: from 0.1% to 10%, preferably from 2% to 7.5%, most preferably from 2 to 5% of octyl methoxycinnamate; from 0.1% to 6%, preferably from 2% to 6%, most preferably from 2% to 4% of oxybenzone; from 0.1% to 5%, preferably from 0.1% to 2%, most preferably from 0.1% to 1% of avobenzone; from 0.1% to 25%, preferably from 2% to 25%, most preferably from 2% to 5% of titanium dioxide; from 0.1% to 25%, preferably from 2% to 25%, most preferably from 2% to 5% of zinc oxide.

An oil or oily material may be present, together with an emulsifier to provide, preferably, an oil-in-water emulsion.

Emollients are often incorporated into cosmetic compositions of the present invention. Levels of such emollients may range from 0.5% to 50%, preferably between 5% and 30% by weight of the total composition. Emollients may be classified under such general chemical categories as esters, fatty acids and alcohols, polyols and hydrocarbons.

Esters may be mono- or di-esters. Acceptable examples of fatty di-esters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, diisopropyl adipate and cetyl octanoate.

Suitable fatty alcohols and acids include those compounds having from 10 to 20 carbon atoms. Especially preferred are such compounds such as cetyl, myristyl, palmitic and stearyl alcohols and acids.

Among the polyols which may serve as emollients are linear and branched chain alkyl polyhydroxyl compounds. For example, propylene glycol, sorbitol and glycerin are preferred. Also useful may be polymeric polyols such as poly-propylene glycol and polyethylene glycol. Butylene and propylene glycol are also especially preferred as penetration enhancers.

Exemplary hydrocarbons which may serve as emollients are those having hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1% to 20% by weight, preferably from about 0.5% to 10% by weight of the composition. Exemplary thickeners are cross-linked polyacrylate materials available under the trademark Carbopol from the B.F. Goodrich Company. Gums may be employed such as xanthan, carrageenan, gelatin, karaya, pectin and locust beans gum.

Powders may be incorporated into the cosmetic composition of the invention. These powders include chalk, talc, kaolin, starch, smectite clays, chemically modified magnesium aluminum silicate, organically modified montmorillonite clay, hydrated aluminum silicate, fumed silica, aluminum starch octenyl succinate and mixtures thereof.

Skin care compositions may include coloring agents, opacifiers and perfumes. Amounts of these other adjunct minor components may range anywhere from 0.001% up to 20% by weight of the composition.

Cosmetic Hair Care Compositions

When the inventive composition is a hair care composition, it acts on the skin of the scalp, increasing the blood flow to the skin of the scalp and the hair roots. Such hair care compositions may be "leave-on" or "rinse-off" products such as shampoos, conditioners, tonics, styling aids, etc.

The inventive hair care compositions typically may include the ingredients described above for skin care compositions and further include one or more surfactant materials and/or one or more conditioning agents.

Surfactant materials are selected from anionic, nonionic, amphoteric or cationic surfactants or mixtures thereof.

Hair conditioning products preferably comprise one or more cationic surfactants. The use of cationic surfactants is especially preferred, because these ingredients are capable of providing conditioning benefits to hair.

Suitable anionic surfactants are the alkyl sulphates, alkyl ether sulphates, alkaryl sulphonates, alkyl succinates, alkyl sulphosuccinates, N-alkoyl sarcosinates, alkyl phosphates, alkyl ether phosphates, alkyl ether carboxylates, and alpha - olefin sulphonates, especially their sodium, magnesium, ammonium and mono-, di- and tri-ethanolamine salts. The alkyl groups generally contain from 8 to 18 carbon atoms and may be unsaturated. The alkyl ether sulphates, alkyl ether phosphates and alkyl ether carboxylates may contain from 1 to 10 ethylene oxide or propylene oxide units per molecule, and preferably contain 2 to 3 ethylene oxide units per molecule.

Examples of suitable anionic surfactants include sodium oleyl succinate, ammonium lauryl sulphosuccinate, ammonium lauryl sulphate, sodium dodecylbenzene sulphonate, triethanolamine dodecylbenzene sulphonate and sodium N-lauryl sarcosinate. The most preferred anionic surfactants are sodium lauryl sulphate, triethanolamine lauryl sulphate, triethanolamine monolauryl phosphate, sodium lauryl ether sulphate 1EO, 2 EO and 3 EO, ammonium lauryl sulphate and ammonium lauryl ether sulphate 1 EO, 2 EO and 3 EO.

The nonionic surfactants suitable for use in the composition of the invention may include condensation products of aliphatic (C8–C18) primary or secondary linear or branched-chain alcohols or phenols with alkylene oxides, usually ethylene oxide and generally 6–30 EO.

Other suitable nonionics include mono- or di-alkyl alkanolamides or alkyl polyglucosides. Examples include coco mono- or di-ethanolamide, cocomonoisopropanolamide, and coco di-glucoside.

The amphoteric surfactants suitable for use in the composition of the invention may include alkyl amine oxides, alkyl betaines, alkyl amidopropyl betaines, alkyl sulphobetaines, alkyl glycinates, alkyl carboxyglycinates, alkyl amphopropionates, alkyl amidopropyl hydroxysultaines, acyl taurates and acyl glutamates wherein the alkyl and acyl groups have from 8 to 18 carbon atoms.

Examples include lauryl amine oxide, cocodimethyl sulphopropyl betaine and preferably lauryl betaine, cocamidopropyl betaine and sodium cocamphopropionate.

Examples of cationic surfactants include: cetyl trimethylammonium chloride, stearyl dimethylbenzyl ammonium chloride, cetylpyridinium chloride, quaternium-5, -31, -18 and mixtures thereof.

The level of surfactant materials in shampoo compositions of the invention is preferably more than 1%, more preferably 2–35% and most preferably from 5 to 30% by weight of the composition. In hair-conditioner products according to the invention the level of cationic surfactants is preferably from 0.01 to 10%, more preferably 0.05 to 5%, most preferably 0.1 to 2% by weight of the composition.

If the hair care composition of the invention comprises in addition to the fluorocarbon materials and the cationic surfactant any additional conditioning agent, this material is preferably chosen from cationic polymers, or quaternised protein hydrolysates.

Suitable cationic polymers include Guar Hydroxypropyltrimoniumchloride, Quaternium-19, -23, -40, -57, poly (dimethyldiallylammoniumchloride), poly (dimethyl butenyl ammonium chloride)-,w- bis (triethanolammonium chloride), Poly (dipropyldiallylammonium chloride), Poly (methyl-beta-propaniodiallyammonium chloride), Poly (diallylpiperidinium chloride), poly (vinyl pyridinium chloride), quaternised poly (vinyl alcohol), quaternised poly (dimethylaminoethylmethacrylate) and mixtures thereof.

Suitable protein derivatives include lauryl dimonium hydroxy propylaminohydrolysed animal protein, available commercially under the tradename LAMEQUAT L, and hydrolysed keratin containing sulphur-bearing amino acids, available commercially under the tradename CROQUAT WKP.

The preferred level of conditioning agents other than perfluoropolyethers and cationic surfactants in compositions of the invention is from 0 to 20%, for example from 0.01 to 10% or from 0.1 to 5% by weight.

The hair care composition of the invention may also include minor amounts of other ingredients commonly found in hair-treatment compositions, such as antibacterial agents, antidandruff agents such as zinc pyridinethione or Octopirox, foam boosters, pearlescers, perfumes, dyes, colouring agents, preservatives, viscosity modifiers, proteins, polymers, buffering agents, polyols and other moisturising agents, herb extracts, mink oil or honey.

Use of the Composition

The composition according to the invention is intended primarily as a cosmetic product for topical application to human skin, especially for increasing the supply of endogenous oxygen to skin and thus preventing or reducing the signs of lined, wrinkled, aged or photodamaged skin, or cellulite or promoting scalp health.

In use, a small quantity of the composition, for example from 1 to 100 ml, is applied to exposed areas of the skin, from a suitable container or applicator and, if necessary, it is then spread over and/or rubbed into the skin using the hand or fingers or a suitable device.

Hair care compositions of the invention are generally applied in an amount of from 1 to 50 mls. Preferred amounts for shampoos are 3 to 5 mls to wet hair. After applying the shampoo, the wet hair is worked to create a lather. The lather may be retained on the head for a short time before rinsing, e.g. from 1 to 4 minutes, or may immediately be rinsed. The treatment may be repeated, if required. For conditioners the preferred dosage is from 8 to 20 mls which is applied to hair after washing or rinsing, whereafter the wet hair is worked and rinsed.

Product Form and Packaging

The composition of the invention can be formulated as a lotion, a fluid cream, or a cream. A lotion or a fluid cream is preferred due to its relatively low viscosity promoting a better spreading of the internal fluorocarbon phase into a more uniform fluorocarbon oil film resulting in an even carbon dioxide delivery to the underlying skin tissue.

The composition can be packaged in a suitable container to suit its viscosity and intended use by the consumer. For example, a lotion or fluid cream can be packaged in a bottle or a roll-ball applicator, or a capsule, or a propellant-driven aerosol device or a container fitted with a pump suitable for finger operation. When the composition is a cream, it can simply be stored in a non-deformable bottle or squeeze container, such as a tube or a lidded jar.

The invention accordingly also provides a closed container containing a cosmetically acceptable composition as herein defined.

The following specific examples further illustrate the invention, but the invention is not limited thereto.

EXAMPLE 1

Endogenous oxygen delivery to the skin was measured using a transcutaneous oxygen monitor (TCM3 transcutaneous $pO_2/pCO_2$ monitor from Radiometer America, Inc.). The instrument's probe contains a platinum cathode as an oxygen sensor electrode and a silver anode as a reference electrode. The current that is created at the electrode in the presence of oxygen is converted by a microcomputer into transcutaneous oxygen values.

To conduct measurements, two test sites were designated on one volar forearm and an adhesive ring was placed at each site. Three drops of propylene glycol contact solution was then added to the inner wells of the rings. Baseline transcutaneous oxygen readings were taken at both sites simultaneously using 2 transcutaneous monitors. After taking baseline readings, the probes were removed from the adhesive rings and the sites were gently blotted dry. Perfluoropolymethylisopropyl ether emulsion (Fomblin, obtained from Brooks Industries Inc) infused with carbon dioxide or Fomblin emulsion control (no carbon dioxide) were prepared. The Fomblin emulsions contained 1.25% of a blend of polyacrylamide with C13–14 isoparaffin and with laureth-7 (an emulsifier under tradename Sepigel 305), the amount of Fomblin as indicated in Table 1, and water in quantity sufficient to 100%. Emulsions were made at room temperature by first adding the Fomblin to water while mixing with an overhead mixer for 10 minutes and then adding the Sepigel 305 while mixing for 10 minutes at 700 rpm.

The infusion was attained by using a carbon dioxide tank with a rubber tube running from the tank to the emulsion: carbon dioxide was piped into the emulsion for 2 minutes while stirring.

Depending on the trial, the sites were treated with either 50, 100 or 200 μl of Fomblin emuslion. One site was treated with Fomblin emulsion with $CO_2$ and the other was treated with Fomblin emulsion control (no $CO_2$). The emulsions were placed at each site using a positive displacement pipette. Within the experiment, the same amount was used for the Fomblin emulsion with $CO_2$ and the Fomblin emulsion control. After 10 minutes, the emulsions were removed from the skin using a cotton swab. The probes were placed back into the adhesive rings and oxygen levels were again measured. Measurements taken after 4, 5 and 6 minutes were divided by their respective baseline readings to determine fold increase in endogenous oxygen over baseline. Statistical significance was determined using a students T-test.

The results that were obtained are summarized in Table 1.

TABLE 1

| Trial # | COLUMN A: Fomblin Emulsion Control – Fold Increase in $pO_2$ Over Baseline (Avg. of 3 time points) | COLUMN B: Fomblin Emulsion + $CO_2$ – Fold Increase in $pO_2$ Over Baseline (Avg. of 3 time points) | p value COLUMN A vs. COLUMN B |
|---|---|---|---|
| 15% Fomblin | | | |
| 1 | 0.50 | 5.4 | 0.0003* |
| 2 | 0.17 | 0.32 | 0.005* |
| 3 | 0.47 | 1.4 | 0.04* |
| 4 | 0.72 | 0.19 | 0.002* (Control is higher) |
| 5 | 0.47 | 1.65 | 0.0004* |
| 30% Fomblin | | | |
| 1 | 0.19 | 1.04 | 0.03* |
| 2 | 0.57 | 1.06 | 0.017* |
| 100% Fomblin | | | |
| 1 | 0.79 | 0.87 | 0.34 |

*statistically significant

The results show that the fluorocarbon infused with carbon dioxide significantly increased transcutaneous oxygen levels over the fluorocarbon emulsion control in six out of eight trials. The composition containing 100% fluorocarbon enriched with carbon dioxide did not significantly increase oxygen levels over the fluorocarbon emulsion control. This may be due to a faster diffusion of air from the atmosphere into the fomblin at the expense of the dissolved carbon dioxide in the case of the pure fomblin. In the case of the fomblin emulsion the vehicle structure may prevent the quick escape of carbon dioxide into the atmosphere thus promoting its release to the underlying tissues by acting like a temporary gas "barrier" or "carbon dioxide sealant". This may indicate the need for using such vehicles as oil-in-water emulsions for the efficient delivery of benefits rather than using neat fluorocarbons.

It should be noted that the results of trial #4 were opposite to the results of the other trials. This may be due to an error in calibrating the instrument prior to trial #4.

EXAMPLE 2

An erythema meter (Diastron) was used to measure spectrophotometrically the level of pinkness on the surface of human skin as an indicator of the level of blood flow. Increased blood flow to the skin typically results in increased pinkness. Two test sites were designated on one volar forearm. 400 μl of fluorocarbon emulsion (either perfluorodecalin or fomblin) enriched with carbon dioxide was placed at one site and perfluorocarbon emulsion control (no $CO_2$) was placed at the other. Perfluorodecalin (MW=462) was obtained from Aldrich. The emulsions were prepared the same as in Example 1. After 5 minutes, the emulsions were removed and 10 consecutive measurements were taken at each site by placing the probe in contact with the skin. Statistical significance was determined using a students T-test. The results that were obtained are summarized in Table 2.

TABLE 2

| Trial # | COLUMN A: | COLUMN B: | p Value: COLUMN A vs. COLUMN B |
|---|---|---|---|
| 1% Fomblin | Fomblin Emulsion Control (Avg. of 10 readings) | Fomblin Emulsion + $CO_2$ (Avg. of 10 readings) | |
| 1 | 8.3 | 15.0 | 0.0005* |
| 30% Fomblin | Fomblin Emulsion Control (Avg. of 10 readings) | Fomblin Emulsion + $CO_2$ (Avg. of 10 readings) | |
| 1 | 7.7 | 17.0 | 0.0005* |
| 2 | 8.1 | 17.9 | 0.0005* |
| 5% Perfluorodecalin | Perfluorodecalin Emulsion Control (Avg. of 10 readings) | Perfluorodecalin Emulsion + $CO_2$ (Avg. of 10 readings) | |
| 1 | 12.7 | 24.6 | 0.0005* |
| 2 | 15.4 | 24.1 | 0.0005* |

*statistically significant

The data in Table 2 shows that pinkness of the skin was significantly greater after treatment with various levels of fluorocarbon emulsions infused with carbon dioxide as compared to the fluorocarbon controls. This demonstrates that blood flow to the skin was higher after treatment with fluorocarbons containing carbon dioxide.

EXAMPLE 3

This example illustrates an oil-in-water cream incorporating the inventive composition.

| | % w/w |
|---|---|
| perfluorodecalin infused with carbon dioxide | 0.15 |
| Mineral oil | 4 |
| Brij 56* | 4 |
| Alfol 16RD* | 4 |
| Triethanolamine | 0.75 |
| Butane-1,3-diol | 3 |
| Xanthan gum | 0.3 |
| Perfume | qs |
| Butylated hydroxy toluene | 0.01 |
| Water | to 100 |

*Brij 56 is cetyl alcohol POE (10)
Alfol 16RD is cetyl alcohol

EXAMPLE 4

This example illustrates a suncare cream incorporating the composition of the invention:

| | % w/w |
|---|---|
| perfluorooctylbromide infused with carbon dioxide | 10 |
| Ursolic acid | 0.1 |
| Glycerylmonostearate | 3 |
| Cetosteryl alcohol | 1.6 |
| Polyoxyethylene-(20)-cetyl alcohol | 1.4 |
| Xanthan gum | 0.5 |
| Parsol 1789 | 1.5 |
| Octyl methoxycinnate (PARSOL MCX) | 7 |
| Perfume | qs |
| Color | qs |
| Water | to 100 |

EXAMPLE 5

The following oil-in-water emulsion within the scope of the invention is prepared:

| chemical name | wt. % |
|---|---|
| perfluoropolymethylisopropyl ether infused with carbon dioxide | 25 |
| glycerin | 1 |
| tetrasodium EDTA | 0.1 |
| cetyl alcohol | 1 |
| stearyl alcohol | 1 |
| mineral oil | 5 |
| polyquaternium 37 | 2 |
| steareth-21 | 1 |
| steareth-2 | 0.5 |
| salicylic acid | 2 |
| triethanolamine | to pH 3.0 |
| water DI | qs to 100% |

EXAMPLE 6

The following oil-in-water emulsion within the scope of the invention is prepared:

| chemical name | wt. % |
|---|---|
| perfluorodecane infused with carbon dioxide | 50 |
| xanthan gum | 0.2 |
| disodium EDTA | 0.1 |
| sodium PCA | 0.5 |
| diazodinyl urea | 0.3 |
| titanium dioxide | 1 |
| stearic acid | 3 |
| cetyl alcohol | 0.5 |
| glyceryl stearate | 0.5 |
| peg-100 stearate | 0.5 |
| steareth-2 | 0.2 |
| lecithin | 0.5 |
| tocopherol | 0.2 |
| octyl methoxycinnamate | 6 |
| green tea extract | 1 |
| triethanolamine | to pH 3.8 |
| Water DI | qs to 100% |

EXAMPLE 7

A typical oil-in-water emulsion within the scope of the invention is as follows:

| chemical name | wt. % |
|---|---|
| perfluorotributylamine infused with carbon dioxide | 30 |
| propylene glycol | 1 |
| glycerin | 1 |
| hydroxyethylcellulose | 0.5 |
| magnesium aluminum silicate | 0.5 |
| imidazolidinyl urea | 0.5 |
| tetrasodium EDTA | 0.05 |
| petrolatum | 2 |
| isopropyl palmitate | 5 |
| cholesterol | 0.5 |
| cetyl alcohol | 0.5 |
| isostearic acid | 3 |
| retinyl palmitate | 0.1 |
| peg-40 stearate | 1 |
| peg-100 stearate | 1 |
| sorbitan stearate | 1 |
| water DI | qs to 100% |

EXAMPLE 8

The following oil-in-water emulsion within the scope of the invention is prepared:

| chemical name | wt. % |
| --- | --- |
| bis-(F-butyl)-ethene infused with carbon dioxide | 60 |
| all-trans retinoic acid | 0.05 |
| light mineral oil | 10 |
| stearoxytrimethylsilane and stearyl alcohol | 5 |
| stearyl stearate | 10 |
| quaternium-15 | 3 |
| peg-22 dodecyl glycol copolymer | 1 |
| sorbitol | 0.5 |
| methyl paraben | 0.2 |
| disodium EDTA | 0.1 |
| butylated hydroxytoluene | 0.1 |
| water DI | qs to 100% |

EXAMPLE 9

The following conditioner composition can be made by heating the water to 80° C. The first five ingredients are added with stirring. The mixture is cooled to 40° C. with stirring. Preservatives, perfume and color are added. The resulting mixture is cooled.

| INGREDIENT | % wt |
| --- | --- |
| Cetyl trimethylammoniumchloride | 0.7 |
| Cetostearyl alcohol | 2.0 |
| Paraffin wax | 1.0 |
| Glycerolmonostearate | 0.7 |
| Perfluoropolyether infused with carbon dioxide | 0.001 |
| Preservative, perfume, color | qs |
| water | to 100 |

EXAMPLE 10

A shampoo of the following formulation can be made by using a simple cold process, whereby all the ingredients are mixed using a paddle stirrer.

| INGREDIENT | % wt |
| --- | --- |
| Sodium Lauryl ether sulphate 2EO | 16.0 |
| Lauryl betaine | 2.0 |
| Jaguar C13S | 0.04 |
| Perfluoropolyether infused with carbon dioxide | 0.003 |
| NaCl | 1.0 |
| Preservative, perfume, colour | qs |
| water | to 100 |

It should be understood that the specific forms of the invention herein illustrated and described are intended to be representative only. Changes, including but not limited to those suggested in this specification, may be made in the illustrated embodiments without departing from the clear teachings of the disclosure. Accordingly, reference should be made to the following appended claims in determining the full scope of the invention.

What is claimed is:

1. A cosmetic skin or hair care oil-in-water emulsion comprising:

i) from about 0.1% to about 70%, by weight of the emulsion of a fluorocarbon infused with carbon dioxide wherein the fluorocarbon is inert, liquid at 25° C. and hydrophobic and is selected from the group consisting of perfluorooctane, perfluorodecane, perfluorodecalin, perfluorooctylbromide, perfluorodecylbromide, perfluorooctyliodide, perfluorotripropylamine, perfluoro-tributylamine, bis-(F-butyl)-ethene and perfluoro-polymethylisopropyl ether;

ii) an ingredient selected from the group consisting of a sunscreen in an amount from 0.1 to 25% by weight; and a cationic conditioning agent in an amount from 0.01 to 10% by weight;

iii) a cosmetically acceptable vehicle.

2. A method of delivering endogenous oxygen to skin, the method comprising applying to skin a cosmetic skin or hair care composition comprising:

i) from about 0.1% to about 70%, by weight of the composition, of a fluorocarbon infused with carbon dioxide wherein the fluorocarbon is inert, liquid at 25° C. and hydrophobic and is selected from the group consisting of perfluorooctane, perfluorodecane, perfluorodecalin, perfluorooctylbromide, perfluorodecylbromide, perfluorooctyliodide, perfluorotripropylamine, perfluoro-tributylamine, bis-(F-butyl)-ethene and perfluoro-polymethylisopropyl ether; and ii) an ingredient selected from the group consisting of a sunscreen in an amount from 0.1 to 25% by weight and a cationic conditioning agent in an amount from 0.01 to 10% by weight; and iii) a cosmetically acceptable vehicle.

3. A method of preparing the emulsion of claim 1, the method comprising infusing fluorocarbon with carbon dioxide and subsequently incorporating the fluorocarbon infused with carbon dioxide into the emulsion.

* * * * *